United States Patent [19]
Javier, Jr. et al.

[11] Patent Number: 5,951,567
[45] Date of Patent: Sep. 14, 1999

[54] INTRODUCER FOR CHANNEL FORMING DEVICE

[75] Inventors: Manuel A. Javier, Jr., Santa Clara; Stephen B. Pearce, Fremont; Randy J. Kesten, Mountain View; Sam G. Payne, Santa Clara, all of Calif.

[73] Assignee: Cardiogenesis Corporation, Sunnyvale, Calif.

[21] Appl. No.: 08/900,208

[22] Filed: Jul. 24, 1997

[51] Int. Cl.⁶ .................................................. A61F 11/00
[52] U.S. Cl. ............................ 606/108; 606/7; 606/107; 606/170; 606/200; 604/18; 604/93
[58] Field of Search ................................. 606/108, 107, 606/127, 159, 167, 170, 198, 200, 7; 640/11, 18, 19, 93; 600/136, 101, 138, 139

[56] References Cited

U.S. PATENT DOCUMENTS

| | | | |
|---|---|---|---|
| 4,552,554 | 11/1985 | Gould et al. ............................... | 604/51 |
| 4,781,690 | 11/1988 | Ishida et al. ............................. | 604/164 |
| 4,926,858 | 5/1990 | Gifford, III et al. ..................... | 606/159 |
| 4,947,864 | 8/1990 | Shockey et al. .......................... | 128/772 |
| 5,071,408 | 12/1991 | Ahmed .................................... | 606/108 |
| 5,188,605 | 2/1993 | Sleep ...................................... | 604/158 |
| 5,725,521 | 3/1998 | Mueller ..................................... | 606/7 |

*Primary Examiner*—Michael Buiz
*Assistant Examiner*—Lien Ngo
*Attorney, Agent, or Firm*—Heller Ehrman White and McAuliffe

[57] ABSTRACT

The invention is directed to an introducer which is formed of a relatively rigid tubular member having an inner lumen and an elongated slot in the distal portion of the introducer. The introducer is particularly suitable for introducing an elongated channel forming device having radially extending arms for limiting the depth of penetration into a guiding or delivery catheter. By pulling the channel forming member into the inner lumen of the introducer, the radially extending arms are bent or folded forwardly into the inner lumen and they remain in this position until they extend out the distal end of the guiding or delivery catheter.

9 Claims, 4 Drawing Sheets

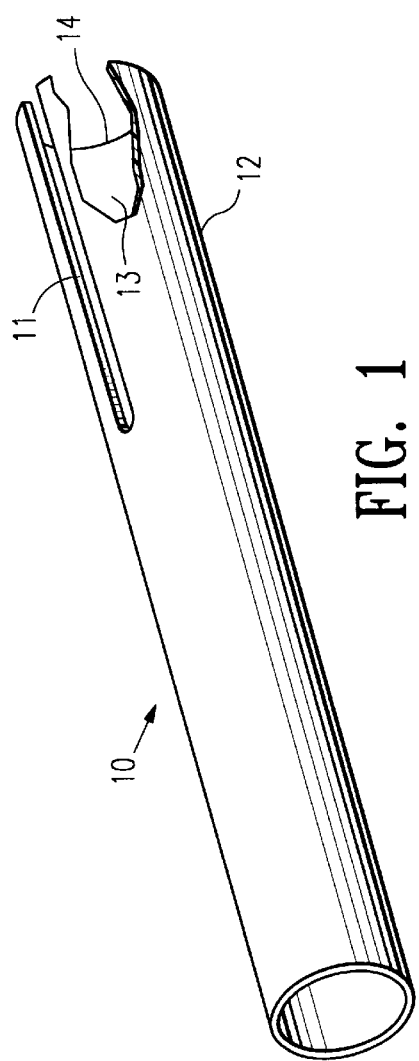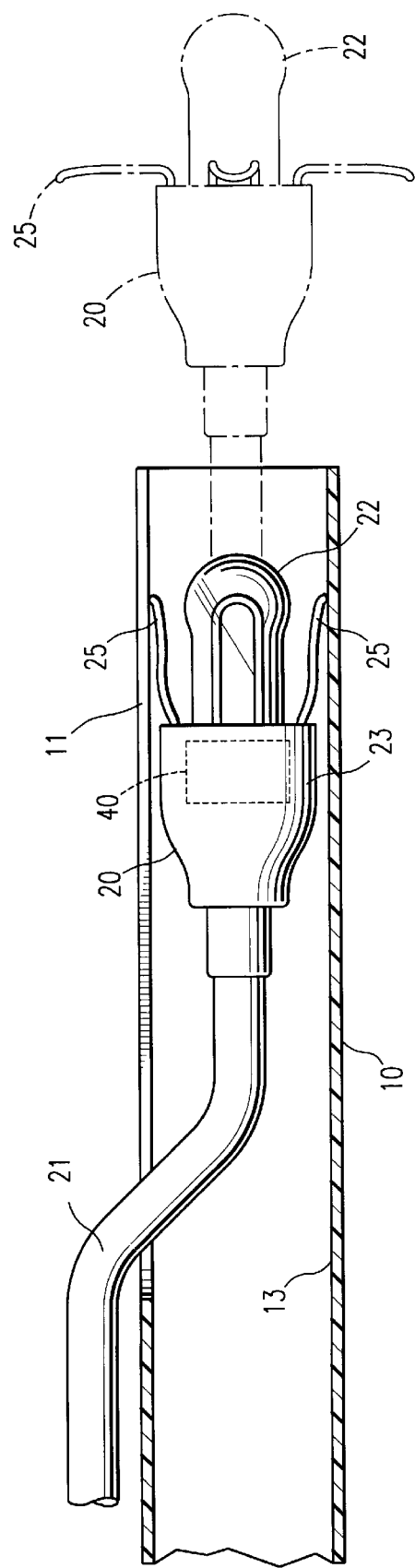

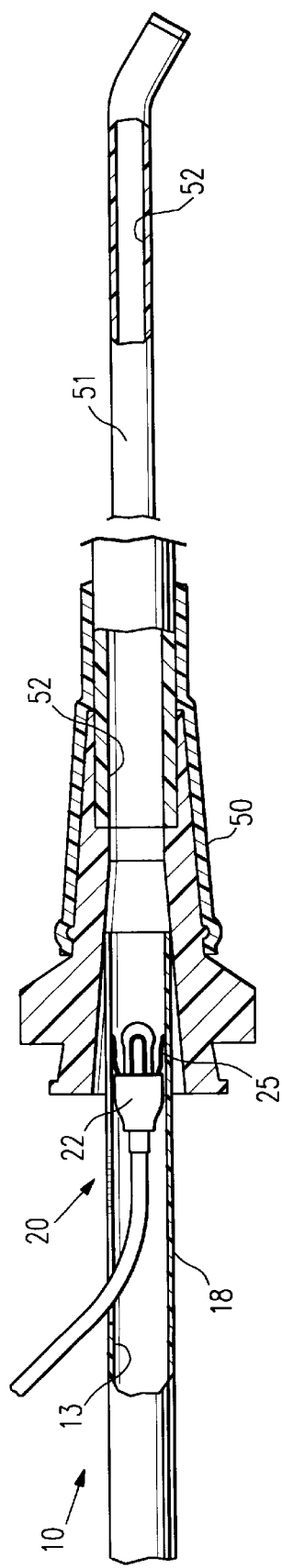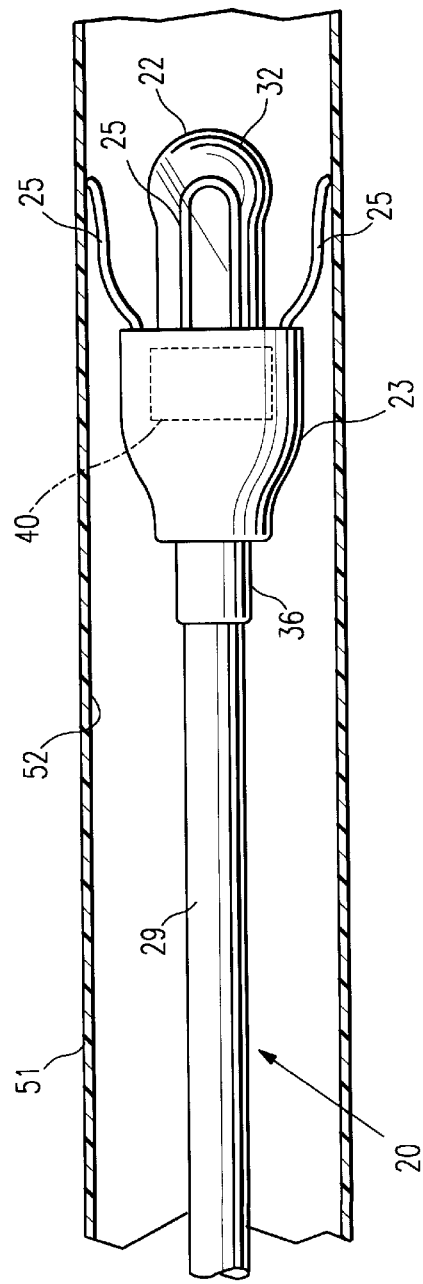
FIG. 8
FIG. 9

INTRODUCER FOR CHANNEL FORMING DEVICE

BACKGROUND OF THE INVENTION

This invention is directed to the formation of one or more channels into the wall of a patient's heart. Such channels may be used to increase blood flow to heart tissue, for the delivery of therapeutic or diagnostic agents to various locations in the patient's heart or for a variety of other utilities.

The formation of a channel in a patient's ventricular wall is called trans myocardial revascularization. The first clinical trials of the trans myocardial revascularization procedure were performed by Mirhoseini et al. See for example the discussions in *Lasers in General Surgery* (Williams & Wilkins; 1989), pp 216–223. Other early disclosures of this procedure are found in an article by Okada et al. in Kobe J. Med. Sci 32, 151–161, October 1986 and in U.S. Pat. No. 4,658,817 (Hardy). These early references describe intraoperative revascularization procedures which require an opening in the chest wall and include formation of the channels through the epicardium.

Copending application Ser. No. 08/361,787, filed Dec. 20, 1994 (Aita et al.), which is incorporated herein in its entirety, describes a system for trans myocardial revascularization which is introduced through the chest wall. In U.S. Pat. No. 5,389,096 (Aita et al.) a percutaneous method is described for forming a channel in a patient's ventricular wall wherein an optical fiber device is advanced through a peripheral artery such as the femoral artery and through the aorta into the patient's left ventricle. Within the left ventricle, the distal end of the optical fiber device is directed toward a desired location on the patient's endocardium and urged against the endocardial surface while a laser beam is emitted from its distal end to form the channel. The depth of penetration of the distal end of the laser device is affected by the force applied by the distal end to the tissue into which the channel is being formed. Because of the nature of the environment, i.e. fluid currents within the heart chamber, the moving interior heart surface and the uneven surface of the patient's endocardium, controlling the force applied to the endocardial tissue by the end of the laser device can be quite difficult. Complete penetration through the ventricular wall from within the ventricular chamber is not desirable.

A system for limiting the penetration of laser type devices is described in co-pending application Ser. No. 08/584,957, filed on Jun. 7, 1995, which is hereby incorporated into this application by reference. However, with the device described in the above copending application, it was found difficult to insert the probe tip of the device into the adapter on the proximal end of the guiding catheter which is used to deliver the laser device into the interior of the patients heart chamber. The present invention minimizes the difficulties with this prior channel forming devices as well as other such devices.

SUMMARY OF THE INVENTION

The present invention is directed to an improved introducer revascularization or channel forming device having bendable penetration limiting means.

The channel forming device with which the introducer of the invention is usable generally includes an elongated shaft with a proximal and distal shaft sections, a means to penetrate a patient's ventricular wall on the distal shaft section and a bendable or foldable means to limit the depth of penetration of the penetration means into heart tissue during the formation of the channel therein. The bendable or foldable means to limit the depth of penetration is preferably at least one radial projecting arm on the distal shaft section spaced proximally from the penetration means to form the channel on the distal shaft section.

The introducer of the invention is an elongated tubular member having proximal and distal sections, a port in the distal end, an inner lumen extending within at least the distal section to the port in the distal end and an elongated slot in the wall of the distal section in communication with the inner lumen extending therein. The slot is wide enough to allow the passage of a portion of the elongated shaft of the channel forming device but is small enough to prevent the passage of the distal shaft section having the penetration limiting means. Typically the slot is about 1 to about 3 inches (2.54–7.6 cm) in length and about 0.015 to about 0.04 inch in width (0.4–1.0 mm). The overall length of the introducer may be from about 3 to about up to about 10 inches or more (7.6–25.4 cm) and is typically about 5 inches (12.7 mm). The diameter of the inner lumen of the introducer must be larger than the maximum outer diameter of the distal tip of the channel forming means which is to be disposed therein and is typically about 0.08 to about 0.15 inch (2.0–3.8 mm).

To use the introducer, typically the elongated shaft of the channel forming means is directed through the slot into the inner lumen within the distal section of the introducer. The proximal portion of the elongated shaft of the channel forming device extending out of the introducer is pulled to pull the distal section of the channel forming device through the port in the distal end of the introducer into the inner lumen. As the distal section is pulled through the distal port into the inner lumen of the introducer, the flexible or bendable arms of the penetration limiting means fold forwardly which allows them to be pulled into the inner lumen as the distal section is pulled into the interior of the introducer. The distal end of the introducer may then be introduced into the adapter on the proximal end of a guiding or delivery catheter and once properly positioned within the interior of the adapter or the lumen of the catheter, the channel forming device may be advanced out the port in the distal end of the introducer and the introducer may then be withdrawn from the proximal end of the adapter, leaving the distal section of the channel forming device within an inner lumen of the guiding or delivery catheter or the adapter connected thereto. The channel forming device may then be further advanced through the catheter until the distal section of the channel forming device extends out of the distal end of the catheter. When the distal section of the channel forming device extends out of the distal end of the guiding or delivery catheter, the folded arm or arms of the penetration limiting means extend out radially as they were before being pulled into the interior of the introducer to act as stops to limit the penetration or forward motion of the operative end of the channel forming device into the ventricular wall during channel formation, which in turns controls the depth of the channel into the ventricular wall. The means to limit the penetration into the ventricular wall may be a plurality of arms, preferably four, which are folded forwardly when the channel forming device is introduced into and advanced within a guiding or delivery catheter to the ventricular chamber, but which expand outwardly when the distal section exits the distal end of the guiding or delivery catheter within the chamber. The stopping arm is spaced from the distal end of the channel forming device the desired penetration distance for the distal tip of the channel forming device. By providing the means to control the depth of penetration, there is less need for concern about the pressure applied by the physician to the channel forming device affecting the depth of penetration which may lead to the complete penetration of the ventricular wall.

The presently preferred channel forming device is an elongated optical fiber with a distal probe tip on the distal end of the optical fiber to control the emission laser radiation therefrom. The distal probe tip preferably has an interior chamber into which the distal extremity of the optical fiber extends and an outer support member or sleeve is secured to the proximal portion of the probe tip and a distal portion of the optical fiber extending out the proximal end of the probe tip to ensure the integrity of the probe tip and optical fiber during the channel forming procedure. The outer support sleeve may be shrunk fit onto the probe tip or it may be bonded by a suitable adhesive. Further details of this construction can be found in copending application Ser. No. 08/482,125, filed on Jun. 7, 1995, which has been incorporated herein by reference.

In a presently preferred device for forming channels in a patient's ventricular wall, the probe tip length is about 3 to about 20 mm and the length of the portion of the probe tip which extends out the distal end of the outer support member is about 1 to about 5 mm. Generally, at least about 1 mm of the proximal portion of the probe tip, preferably at least about 2 mm thereof, is secured by the outer support member to ensure holding the probe tip in a secured relationship with the optical fiber in the case of a fractured probe tip. The proximal portion of the outer support member secured to the distal end of the optical fiber should be at least about the same length as described above for the distal portion, although generally it will be longer. For an intraoperative device which is designed to form channels from the exterior of the patient's heart the dimensions may be significantly larger than those set forth above for a percutaneous device.

An adapter is provided on the proximal end of the laser device which is configured to connect the proximal end of the optical fiber in an optical transmission relationship with a laser source.

These and other advantages of the invention will become more apparent from the following detailed description of the invention, when taken in conjunction with the accompanying exemplary drawings.

BRIEF DESCRIPTION OF THE DRAWINGS

FIG. 1 is a perspective view of an introducer embodying features of the invention.

FIG. 2 is an elevational view of the introducer shown in FIG. 1, partially in section with the probe tip of a laser device disposed within the inner lumen of the introducer device.

FIG. 8 is an elevational view, partially in section, of a guiding catheter with the introducer and laser device shown in FIG. 2 being introduced into an adapter on the proximal end of the guiding catheter.

FIG. 9 is an elevational view, partially in section, illustrating the passage of the laser device through the interior of the guiding catheter.

DETAILED DESCRIPTION OF THE INVENTION

Figure 3:
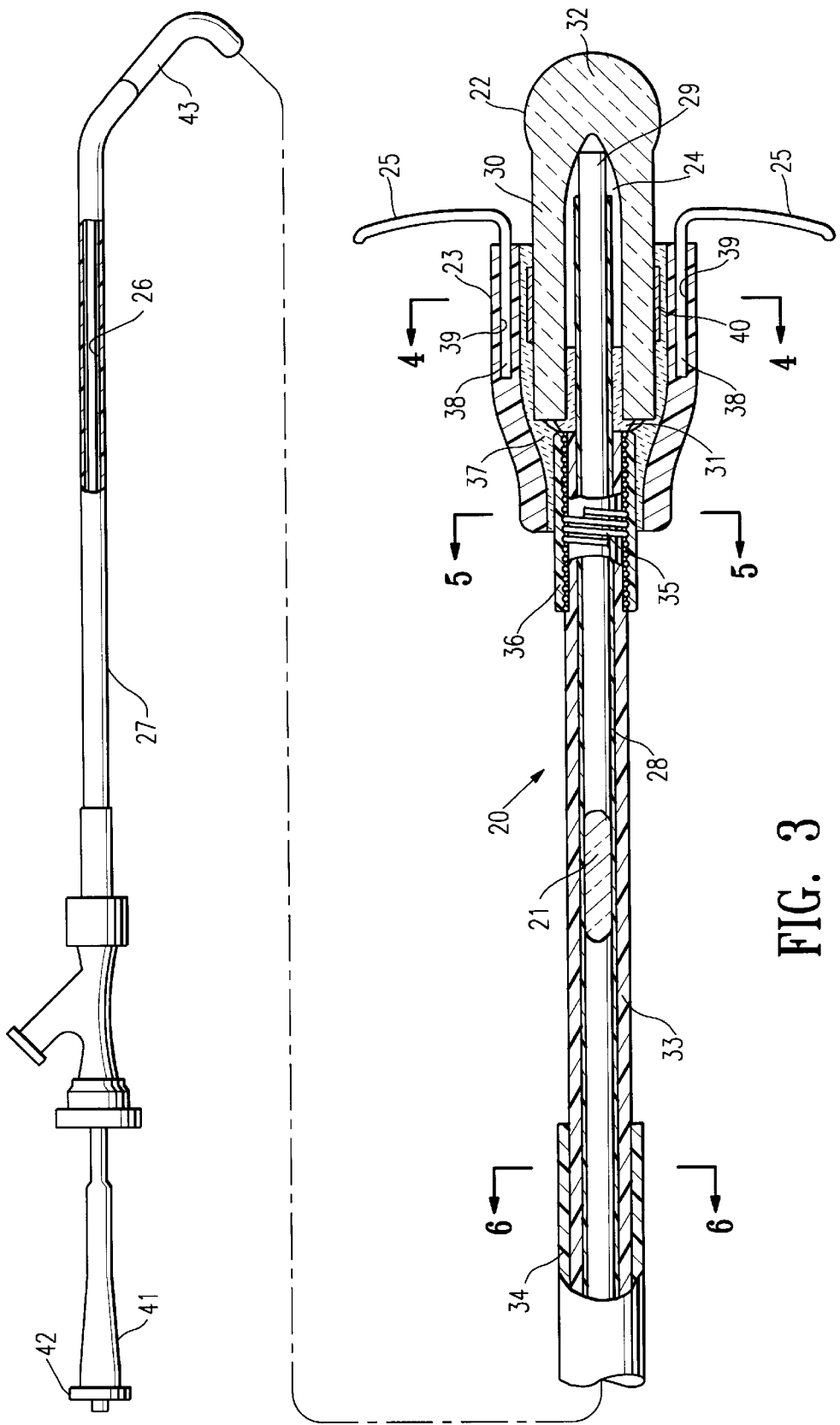
FIG. 3 is an elevational view, partially in section, of a channel forming device embodying features of the present invention.

An introducer 10 embodying features of the invention is illustrated in FIG. 1 which has slot 11 in the distal section 12 opening into an inner lumen 13 provided at least in the distal section, a port 14 in the distal end and a port 15 in the proximal end.

In FIG. 2 an optical fiber based channel forming device 20 is shown with its distal section disposed within the inner lumen 13 of the introducer 10 and its proximal section extending through the slot 11 and generally running parallel to the introducer. The distal section of the channel forming device disposed out of the introducer before it is pulled into the inner lumen 13 is shown in phantom.

Figure 5:
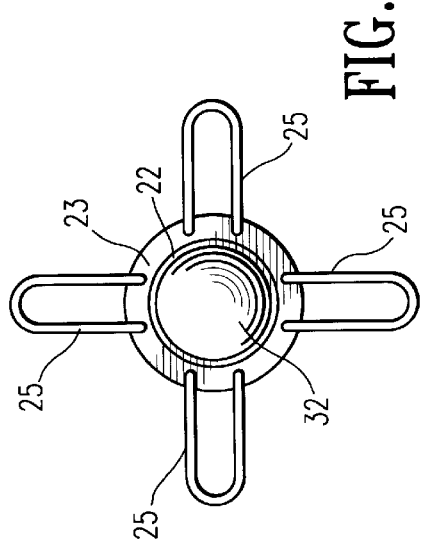
FIG. 5 is a transverse cross-sectional view of the channel forming device shown in FIG. 3, taken along the lines 5—5.
Figure 7:
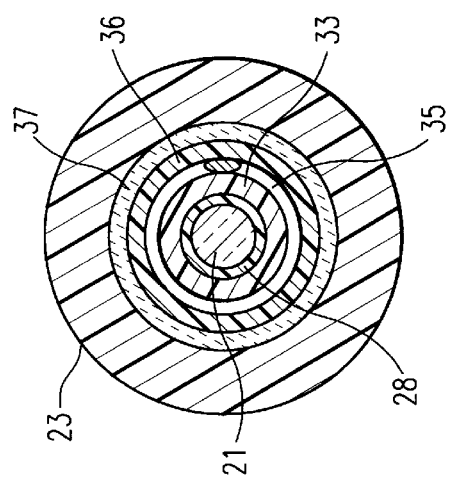
FIG. 7 is an end view of the device shown in FIG. 3.
Figure 4:
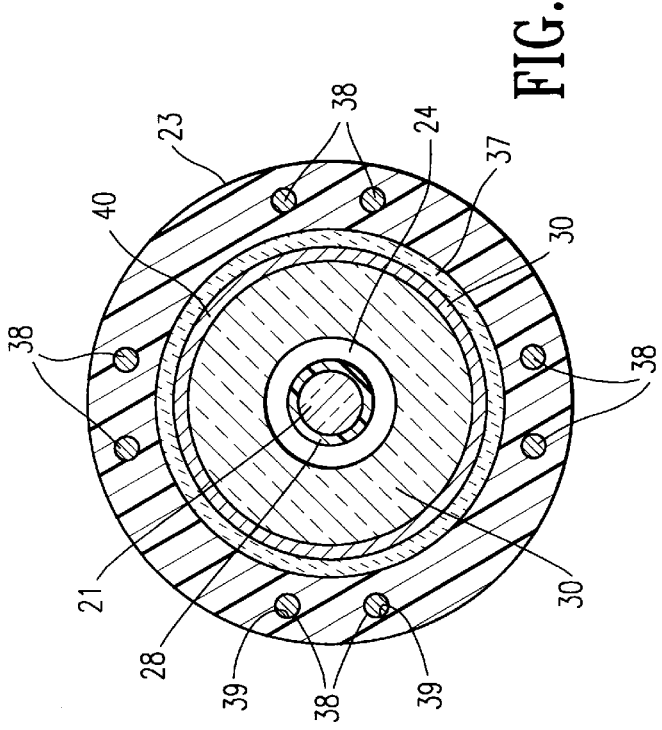
FIG. 4 is a transverse cross-sectional view of the channel forming device shown in FIG. 3, taken along the lines 4—4.
Figure 6:
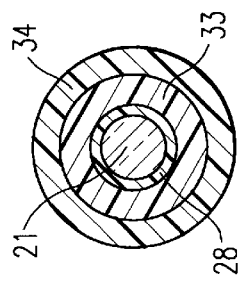
FIG. 6 is a transverse cross-sectional view of the channel forming device shown in FIG. 3, taken along the lines 6—6.

FIGS. 2–7 depict a presently preferred channel forming device 20 which includes an elongated optical fiber 21, an elongated probe tip 22 disposed about and secured to the distal extremity of the optical fiber, and an outer tubular support member or sleeve 23 secured to the exterior of the proximal extremity of the probe tip 22 and a distal portion of the optical fiber which is not disposed in the interior chamber 24 of the probe tip 22. A plurality of radially extending arms 25 are provided proximal to the distal end of the probe tip to limit the penetration of the probe tip into the patient's ventricular wall as a channel is being formed. The channel forming device 20 is slidably disposed within the inner lumen 26 of delivery catheter 27. A positioning catheter (not shown) may be disposed between channel forming device 20 and the delivery catheter 27 which can facilitate closer placement of the probe tip 22 onto the endocardium of the ventricular wall, as described in copending application Ser. No. 08/438,743, filed on May 10, 1995. This latter application is incorporated herein in its entirety by reference.

The exterior of the optical fiber 21 is provided with a fluoropolymeric cladding 28 along its length except for a distal portion 29 which extends into the distal end of the interior chamber 24 of the probe tip 22.

The elongated probe tip 22 has a cylindrical body 30 which is bonded to the distal end of the optical fiber 21 by adhesive 31. The probe tip 22 has a distal end 32 which acts as a lens to control laser energy emitted from the distal end of the optical fiber to a location immediately distal to the lens to ensure formation a channel of a desired size in the ventricular wall. A fluoropolymer buffer 33 is disposed about the optical fiber 21 proximal to the body of adhesive 31 and extends proximally along essentially the remainder of the optical fiber. An outer jacket 34 is disposed about the fluoropolymer buffer 33 along most of its length, and terminates about 10 cm from the proximal end of the outer tubular support member 23. A helical coil 35, formed of high strength material such as stainless steel, NITINOL and the like, is disposed between the fluoropolymer buffer 33 and the proximal end of the outer tubular support member 23 and has a jacket 36 formed of suitable plastic material such as polyethylene terephthalate (PET). The coil 35 and jacket 36 together facilitate an effective bond between the fluoropolymer buffer 33 and the outer tubular support member 23. Adhesive 37 bonds the outer tubular support member 23 to the coil jacket 36. Alternatively, the fluoropolymer buffer 33 and the outer tubular support member 23 may be joined by a threader interconnection.

The radially extending arms 25 are U-shaped flexible wire members with the free ends 38 embedded within the outer tubular support member 23. Preferably, the outer tubular support member 23 is provided with lumens 39 which receive the free ends 38 of the arms 25 and are secured therein by a suitable adhesive (not shown). Other means may be utilized to secure the free ends 38 of the arms 25 between the probe tip 22 and the exterior of the outer tubular support member 23. When the arms 25 extend out radially, they act to limit the penetration of the probe tip 22 into the channel as it is being formed in the ventricular wall and thus controls the depth of the channel formed.

A radiopaque band 40 may be secured to the exterior of the cylindrical body 30 by the adhesive 37 to facilitate the fluoroscopic observation of the probe tip 22 while placing the distal probe tip 22 in a desired location within the patient's heart chamber and during the channel forming procedure. The band may be formed of a wide variety of metallic components including gold, platinum, iridium, alloys thereof and the like.

The proximal end of the channel forming device 20 is provided with a connector 41 which has a rotatable, internally threaded collar 42 which facilitates an optical connection of the proximal end of the optical fiber 21 with a source of laser energy.

The distal end 43 of the delivery catheter 27 is preferably preformed into a desired shape which when positioned within a patient's heart chamber, directs the distal extremity of the optical fiber 21 and the probe tip 22 onto a desired location on the surface of the free ventricular wall of the patient's heart. If a positioning catheter is employed, its distal end may likewise be formed with a desirable shape to facilitate directing the probe tip to the desired location.

The introducer of the present invention is preferably relatively rigid and is formed of a metallic material such as stainless steel or a NiTi alloy. The various components of the channel forming device 20 may be formed of a wide variety of conventional materials used in the construction of intravascular catheters and other intracorporeal devices. The contemplated materials of construction and the sources thereof for one presently preferred embodiment are provided in the following table.

| COMPONENT | MATERIAL | SUPPLIER |
| --- | --- | --- |
| Proximal Optical Connector | Various | Amphenol Corporation Lisle, IL and Spectran[1] Specialty Optics, Co. Avon, CT |
| Jacket (34) | Pebax 7233 tubing with 3% $TiO_2$ | North American Infinity Extrusions and Engineering, Inc. Santa Clara, CA 95054 |
| Tubular Support Member (23) | Nylon 12, 1/8" | Guidant Corporation 3200 Lakeside Dr. Santa Clara, CA 95052 |
| UV-Cured Adhesive (30) | Urethane Oligomer (197-M) Acrylate | Dymax Corp. Torrington, CT |
| PET Shrink Tubing (36) | Polyethylene Terephthalate | Advanced Polymers, Inc. Salem, NH |
| Probe Tip (22) | Fused Quartz | Polymicro Technologies, Inc. Phoeniz, AZ |
| Optical Fiber Buffer (33) | Tefzel ® | Spectran Specialty Optic Co. Avon, CT |
| Optical Fiber Cladding (28) | Proprietary Fluoropolymer Acrylate | Spectran Specialty Optic Co. Avon, CT |
| Optical Fiber (21) | Fused Silica (Low $OH^-$) | Spectran Specialty Optic Co. Avon, CT |

The overall length of a channel forming device in accordance with the present invention is about 200 to about 400 cm with a typical value being about 350 cm. The actual length being determined by the location of the source of laser energy. The operative distal portion of the device, i.e. the portion which is inserted into the patient is about 10 to about 60 cm in length. The probe tip for percutaneous use is about 3 to about 10 mm in length with the length of the exposed distal portion which extends out of the tubular support member being about 1 to about 5 mm, preferably about 2 to about 4 mm. The outer diameter of the probe tip is about 1 to about 3 mm, preferably about 1.5 to about 2 mm, and is measured at the widest portion of the bulbous tip which forms the lens. The outer diameter of the coating or jacket on the probe tip is essentially the same as the bulbous tip. The length of the outer tubular support member is about 0.3 to about 40 cm, preferably about 0.5 to about 30 cm and the length of the radial extension of the arms 15 is about 0.5 to about 2 mm.

As is shown in FIG. 8, the introducer 10 is inserted into the proximal end of the adapter 50 on the proximal end of guiding catheter 51 with the probe tip 22 of optical fiber device 20 disposed within the inner lumen 13 of the introducer as shown in FIG. 2. The arms 25 are folded forwardly and the probe tip 22 is advanced into the lumen 52 extending through the adapter 50 and guiding catheter 51 with the arms 25 in the forwardly folded condition. When the probe tip 22 is advanced sufficiently within the inner lumen 52 as shown in FIG. 9, the introducer may then be withdrawn. The delivery catheter 27 may be advanced through the guiding catheter 72 into the patient's heart chamber.

Preferably, the arms 25 are formed of a NiTi alloy having pseudoelastic characteristics at body temperature to facilitate the folding thereof and the radial expansion thereof once the probe tip 22 extends out of the distal end of the guiding catheter 51. Folding the arms 25 forwardly from their radial positions causes the stress induced transformation of the austenite phase of the NiTi alloy in the bent portions to the martensite phase and release of the arms from the bent position to allow for their radial expansion causes the transformation of the martensite phase back to the austenite phase.

Although individual features of embodiments of the invention may be shown in some of the drawings and not in others, those skilled in the art will recognize that individual features of one embodiment of the invention can be combined with any or all the features of another embodiment. Moreover, while the present invention has been described herein primarily in terms of a laser based channel forming device which is percutaneously introduced into the patient's vascular system and then advanced therein until the operative end is disposed within a chamber of the patient's heart, those skilled in the art will recognize that the device of the invention may be utilized with a variety of non-laser channel forming devices. See for example those non-laser devices described in co-pending application Ser. No. 08/517,499, filed on Aug. 9, 1995, which is incorporated herein in its entirety. Other modifications and improvements may be made to the invention without departing from the scope thereof.

What is claimed is:

1. An elongated therapeutic or diagnostic assembly comprising:
   a tubular introducer device with a proximal and distal portion, an open distal end, an inner lumen extending therein to the open distal end, a wall in the distal section defining at least in part the inner lumen extending therein and a slot in the wall in the distal portion which opens to the inner lumen extending therein and extends distally to the open distal end of the device; and a revascularization device having an elongated shaft, and an operating distal portion having at least one radially expandable arm, the operating distal portion being disposed within the inner lumen of the introducer device in the distal portion thereof with the expandable arm in a folded condition within the inner lumen such that the operating distal portion has a smaller transverse dimension than a transverse dimension of the inner lumen of the tubular introducer device, and the elongated shaft extending at least in part through the slot in the introducer device.

2. The assembly of claim 1 wherein the wall of the distal portion of the introducer device is diametrically rigid.

3. An elongated introducer comprising a tubular introducer member which is configured for introduction of a revascularization device, and which has a proximal portion and a distal portion, a port in a distal end of the distal portion, an inner lumen having an inner diameter of between about 0.080 and 0.150 inches extending therein to the port in the distal end and a slot in a wall of the distal portion which opens to the inner lumen extending therein and extends to the distal end of the distal portion, the slot being configured to slidably accept an elongated shaft of the revascularization device such that when the elongated shaft is proximally loaded into the slot, an expandable arm on an operating distal portion of the revascularization device can be folded to a smaller transverse dimension than a transverse dimension of the inner lumen of the tubular introducer member.

4. The elongated introducer of claim 3 wherein the distal portion thereof is diametrically rigid.

5. The elongated introducer of claim 3 which is formed of a metallic material.

6. The elongated introducer of claim 3 which has a length of about 3 to about 10 inches.

7. The elongated introducer of claim 3 wherein the slot has a length of about 1 to about 3 inches.

8. A method of introducing a revascularization device having an elongated shaft, a proximal portion and a distal portion having at least one radially expandable arm into the proximal end of a guiding catheter comprising:

a) providing an elongated introducer including a tubular introducer member with a proximal and distal portion, an open distal end, an inner lumen extending therein to the open distal end, a wall in the distal section defining at least in part the inner lumen extending therein, and a slot in the wall in the distal portion which opens to the inner lumen extending therein and extends distally to the open distal end of the device;

b) introducing the elongated shaft of the revascularization device into the inner lumen and slot of the introducer such that the elongated shaft of the revascularization device extends out the slot exteriorly to the introducer and effecting relative longitudinal movement between the introducer and the revascularization device until the distal portion of the revascularization device with at least one expandable arm is disposed within the inner lumen of the introducer with the at least one expandable arm folded forwardly to the port in the distal end of the introducer;

c) inserting the distal end of the introducer into the proximal end of the guiding catheter; and d) advancing the revascularization device out of the distal end of the introducer into the inner lumen of the guiding catheter.

9. The method of claim 8 wherein introducer is withdrawn from the proximal end of the guiding catheter leaving the distal end of the intravascular device within the inner lumen of the guiding catheter.

* * * * *